United States Patent [19]

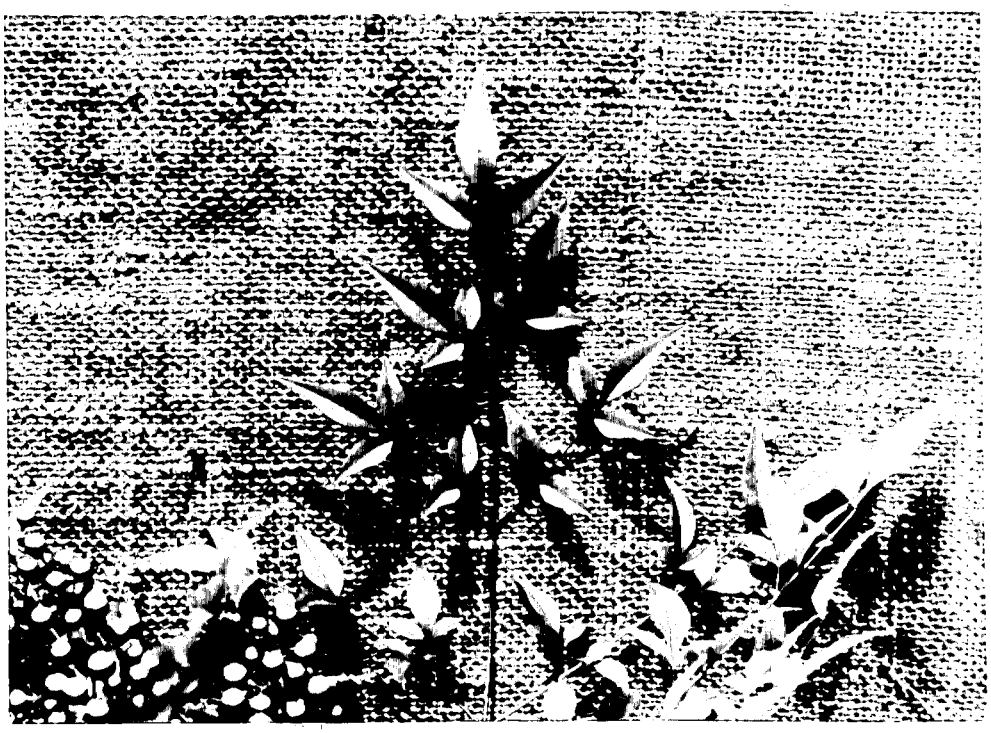
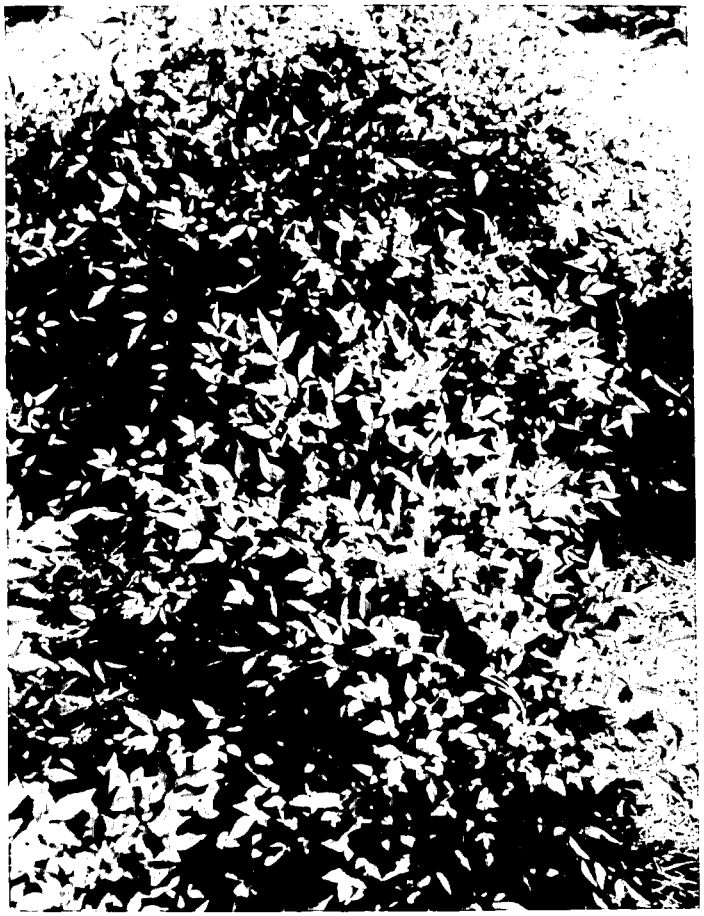

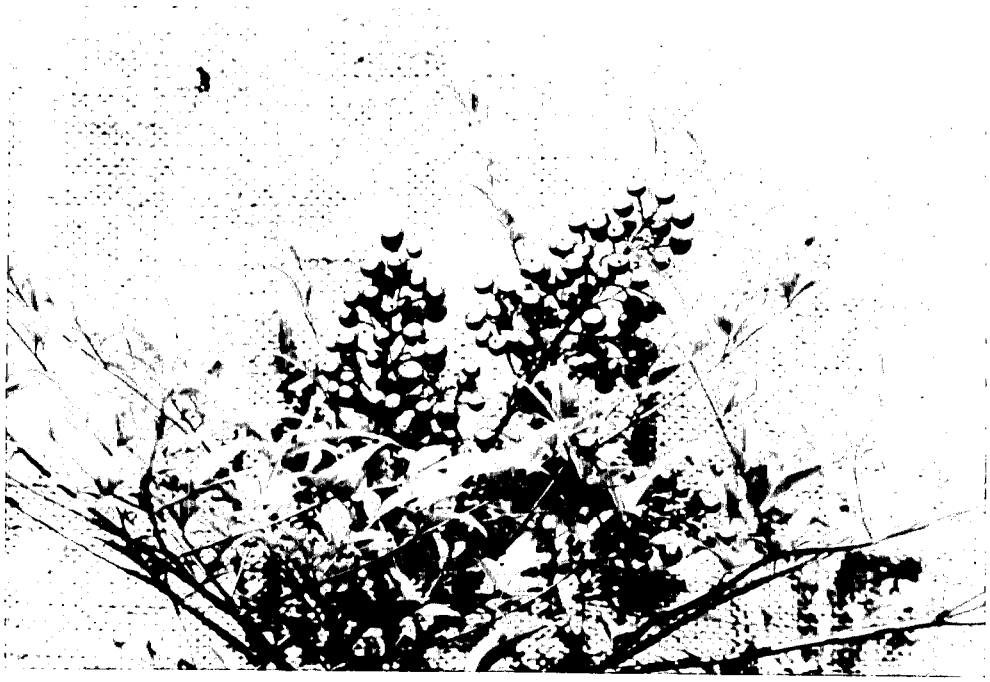
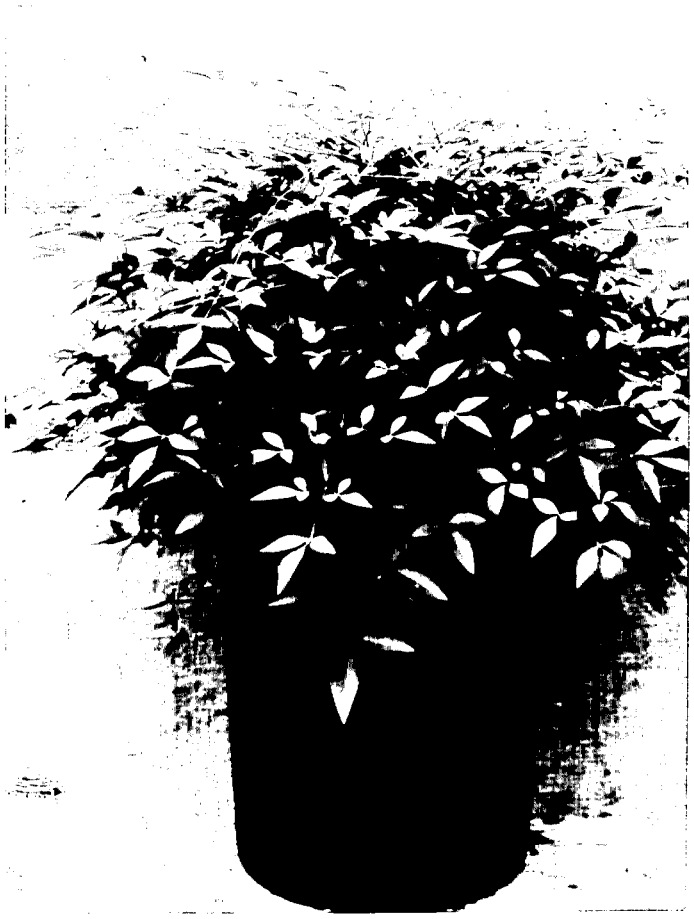

Rushing

[11] Patent Number: Plant 5,560

[45] Date of Patent: Sep. 24, 1985

[54] *NANDINA DOMESTICA* THUNB. CALLED LOWBOY

[76] Inventor: Ralph C. Rushing, Rte. 1, Box 33, Semmes, Ala. 36575

[21] Appl. No.: 553,532

[22] Filed: Nov. 18, 1983

[51] Int. Cl.[4] ..... A01H 5/00

[52] U.S. Cl. ..... Plt./54

[58] Field of Search ..... Plt./54

[56] References Cited

PUBLICATIONS

Wholesale Catalog for 1977, Monrovia Nsy. Co., Azusa, CA.

*Primary Examiner*—Robert E. Bagwill

*Attorney, Agent, or Firm*—Wm. A. Snow

[57] ABSTRACT

A new variety of *Nandina domestica* Thunb. distinguished by a new and improved combination of characteristics never previously exhibited in a heavenly bamboo of new leaves of a rich bronze that change to a metallic bluish green at maturity and in winter develop a uniform reddish purple tint, densely branched, mounded spreading habit and stoloniferous growth, ranging in size from two to three feet in height and two and one half to four feet wide.

4 Drawing Figures

BACKGROUND OF THE NEW PLANT

This new variety of *Nandina domestica,* origin unknown, was selected from seedlings of *Nandina domestica* maintained in the Rushing Nursery at Semmes, Ala. Asexual propagation of my new plant by cuttings has been under my direction for the past year to test stability and determine worthiness for commercial exploitation. This new variety has shown a dense mounded spreading habit with the ultimate size being from two to three feet high and two and one-half to four feet wide.

DESCRIPTION OF THE DRAWINGS

This new variety of *Nandina domestica* Thunb. is illustrated by the accompanying photographic prints, in which:

The first sheet, upper photograph discloses the winter color of my new variety and fruit texture. The lower photograph discloses the spreading, mounding growth habit.

The second sheet, upper photograph discloses the fruit and winter leaves. The lower drawing discloses the summer foliage.

The colors shown are photographically as nearly true as is reasonably possible to obtain by conventional photographic procedures.

DETAILED DESCRIPTION OF THE NEW PLANT

The following is a detailed description of my new variety of *Nandina domestica* based on observations made of plants grown in greenhouses on raised benches and cultured according to conventional greenhouse procedures. The color designations are according to The R.H.S. Colour Chart of The Royal Horticultural Society, published in collaboration with the British Colour Council at London, England, except where color terms of dictionary significance are obvious.

THE PLANT

Origin: Seedling.

Parentage: Unknown seedling of *Nandina domestica* (heavenly bamboo or nandina).

Classification:

*Botanic.*—*Nandina domestica.*

Form: Bush.

Height: 2 to 3 feet.

Width: 2½ to 4 feet.

Growth: Stoloniferous; dense, compact, mounded spreading habit. In Semmes, Ala., there is more-or-less continuous growth from June to August.

Foliage: Abundant in quantity.

*Size of leaf.*—10 To 16 inches long; 16 to 24 inches wide.

*Leaflets.*—½ To 2 inches long; 8 to 12 inches wide.

*Texture.*—Somewhat leathery.

*Shape of leaf.*—Tripinnately compound leaflets, subsessile, elliptic-lanceolate, cuneate, prominent midveins, secondary veins scarcely noticeable. Leaflets composed of up to 170, ½ to 2 inches long, one-half the size of species.

*Color.*—Bronze when emerging on new growth. Reddish Purple in winter, R.H.S. 53B. Color changes occur as leaves mature and the time of change is dependent on climatic conditions. The bronze color is mixed with transitional colors with the mature rich metallic upper leaf color R.H.S. 46A and the under side of the leaf color is R.H.S. 48B.

THE FLOWER

Blooming habit: May and June.

Size: ¼ inches in diameter. 3 to 5 inches long and 1½ to 2½ inches wide panicles. The panicles are sparse compared with the species.

Buds: Small, nondescript, hidden by ensheathing base of the petiole, only visible when leaf is removed.

*Color.*—Creamy White, R.H.S. 155A.

FRUIT

Shape: Round only on fully matured plants in generally three to four years.

Size: When present on mature plant, about ¼ inches in diameter, two seeded, bright red berry.

Resistance to disease: Is disease resistant and resistant also to insects. Initially the fruit develops a metallic color and by late September-October is fully colored and persists on the plant throughout the winter months.

| Characteristic | Applicant | Harbor Dwarf |
|---|---|---|
| Height | 60–90 cm. | 30–45 cm. |
| Width | 76–122 cm. | 30–45 cm. |
| Leaf | 25–41 cm. long<br>41–61 cm. wide | 20–25 cm. long |
| Leaflets | 1.3–5 cm. long<br>20–30 cm. wide | 2–6 cm. long<br>12–20 cm. wide |
| Berrying | abundant on mature plant | sparingly produced |
| Winter Color | Reddish purple | Orange to bronzy red |

The advantages of this new variety are (1) new leaves of rich bronze that change to metallic bluish green at maturity and in winter to a uniform reddish purple tint; (2) a distinctive, dense mounded spreading habit with ultimate size ranging from two to three feet high and two and one-half to four feet wide; (3) stoloniferous growth that results in a compact, dense plant with no tendency to legginess or open growth habit that is typical for species; (4) tripinnately compound leaves ten to sixteen inches long and sixteen to twenty-four inches in width composed of up to 170, one-half to two inches long entire leaflets, which is about one-half the size of the species; (5) creamy white flowers that are sparsely borne in three to five inches long and one and one-half to two and one-half inches wide panicles during May-June, the flowers being not as abundant as the species but can be showy since they are dispersed over a much smaller framework, flowers appearing only on two to three year old container grown plants; (6) the one-fourth inch rounded, bright red fruit ripens in October and may persist through the winter, the entire fructescence being usually dense with fruit on mature plants; (7) easy to root from cuttings collected in July-August or by division at any time; (8) the moderate growth rate under normal fertilizer and moisture conditions; in one year, a plant will fill a standard one-gallon nursery container and be full and dense as described herein; and (9) freedom from disease and insects.

The present plant is readily distinguishable from other Nandina as the Nandina described herein does not have the same characteristics as other Nandina in bearing, color or growth as described in horticultural literature. Also, it does not grow eight feet in height but rather dense, broad-mounded of stoloniferous nature.

I claim:

1. A new and unique variety of heavenly bamboo or Nandina as herein shown and described, characterized by its dense broad-mounded growth habit, stoloniferous nature, bronze to metallic bluish green to reddish purple winter color foliage, creamy white flowers, bright red fruit, adaptability to extreme soil and cultural conditions, the leaves, flowers and fruit being about one-third to one-half the mature size of those for the typical species Nandina; rooted cuttings or divisions will fill a one-gallon container in two seasons, the dense, compact, mounded growth habit will fill numerous landscape needs for missing low-hedging groupings and foundation plantings, requiring less maintenance, especially pruning, than the species; and freedom from disease and insects with wide soil tolerance.

* * * * *